United States Patent [19]

Jacques et al.

[11] 4,436,669

[45] Mar. 13, 1984

[54] PREPARATION OF AROMATIC/ALIPHATIC NITRILES

[75] Inventors: Roland Jacques, Ales; Michel Reppelin, Collonges-au-Mont-d'Or; Laurent Seigneurin, Salindres, all of France

[73] Assignee: Rhone-Poulenc Specialites Chimiques, Courbevoie, France

[21] Appl. No.: 378,191

[22] Filed: May 14, 1982

[30] Foreign Application Priority Data

May 15, 1981 [FR] France .................................. 81 09694

[51] Int. Cl.³ ............................................ C07C 120/10
[52] U.S. Cl. .................................. 260/465 B; 502/224
[58] Field of Search .................... 260/465 B; 252/441

[56] References Cited

U.S. PATENT DOCUMENTS 4,324,698  4/1982  Lewis et al. .................... 252/455 Z

FOREIGN PATENT DOCUMENTS 1250165  11/1960  France .

Primary Examiner—Dolph H. Torrence
Attorney, Agent, or Firm—Burns, Doane, Swecker & Mathis

[57] ABSTRACT

Aromatic/aliphatic nitriles having the formula:

$$Ar-A-CN \quad (I)$$

wherein Ar is phenyl or substituted phenyl and A is a direct chemical bond or a hydrocarbon having from 1 to 6 carbon atoms, are conveniently prepared by heating to a temperature ranging from about 450° C. to about 550° C. a formamide or formanilide having the formula:

$$Ar-A-NHCHO \quad (II)$$

or an amide having the formula $$Ar-A-CONH_2 \quad (III)$$

in the presence of a fluorinated siliceous catalyst, said catalyst having been prepared by (i) impregnating a particulate silica containing from about 0.05 to about 2% by weight of fluorine, expressed as $F^-$ bonded to the silica, with a dilute aqueous solution of hydrofluoric acid, said hydrofluoric acid solution having a concentration in HF of less than about 5% by weight, and the ratio by weight of the hydrofluoric acid contained in said aqueous solution thereof to the silica being less than about 5%, followed by (ii) drying the catalyst thus impregnated.

18 Claims, No Drawings

PREPARATION OF AROMATIC/ALIPHATIC NITRILES

BACKGROUND OF THE INVENTION

1. Field of the Invention

The present invention relates to the preparation of aromatic or aliphatic nitriles, and, more especially, to the preparation of nitriles having the general formula:

$$Ar-A-CN \qquad (I)$$

wherein Ar represents a substituted or unsubstituted benzene radical and A represents a direct chemical bond or a hydrocarbon radical having from 1 to 6 carbon atoms, from formamides or formanilides having the general formula:

$$Ar-A-NHCHO \qquad (II)$$

or amides having the general formula:

$$Ar-A-CONH_2 \qquad (III)$$

wherein Ar and A are as above defined.

2. Description of the Prior Art

It is known to this art, from French Pat. No. 1,250,165, to prepare nitriles from compounds of the aforesaid type (II) by reactively contacting the same, at a temperature ranging from 460° to 560° C., and in the gaseous phase, with a catalyst comprising active silicic acid or silicates containing a metal oxide.

Nonetheless, carrying out the subject reaction with catalysts of the type described in the aforecited French patent evidences that the selectivity realized is not sufficient for optimal industrial utilization of the process. Furthermore, when nitriles of the Formula I are desired, wherein the radical Ar bears a fluorine substituent, the process promotes the formation of heavy by-products which shortens the life of the catalyst by encrusting its surface, and defluorination reactions too are observed, resulting in compounds which are extremely difficult to separate from the desired product.

SUMMARY OF THE INVENTION

Accordingly, a major object of the present invention is the provision of an improved process for the preparation of aromatic or aliphatic nitriles, which improved process is conspicuously devoid of those disadvantages and drawbacks to date characterizing the state of this art.

Another object of the present invention is the provision of an improved process for the preparation of aromatic or aliphatic nitriles from amides having the Formula (III).

Briefly, the present invention features the preparation of aromatic or aliphatic nitriles having the formula:

$$Ar-A-CN \qquad (I)$$

wherein Ar represents a substituted or unsubstituted benzene radical and A represents a direct chemical bond or a hydrocarbon radical having from 1 to 6 carbon atoms, by heating to a temperature ranging from about 450° C. to about 550° C. a formamide or a formanilide having the formula:

$$Ar-A-NHCHO \qquad (II)$$

or an amide having the formula:

$$Ar-A-CONH_2 \qquad (III)$$

wherein Ar and A are as above defined, in the presence of a catalyst prepared by the impregnation with a dilute aqueous solution of hydrofluoric acid having an HF concentration of less than about 5% by weight, of a silica containing about 0.05 to about 2% by weight of fluorine, expressed as $F^-$ bonded to the silica, the ratio by weight of the hydrofluoric acid contained in the aqueous solution to the silica being less than about 5%, followed by the subsequent drying thereof.

By "fluorine bonded to the silica" as utilized herein, there is intended fluorine which is not combined in the known forms of fluosilicates or fluorides.

DETAILED DESCRIPTION OF THE INVENTION

More particularly according to this invention, by "impregnation of the silica" there is intended the contacting of the silica with an aqueous solution of hydrofluoric acid.

And in a preferred embodiment of the invention, such impregnation is carried out by soaking the silica in the aqueous solution of hydrofluoric acid.

In another preferred embodiment of the invention, such impregnation is carried out by atomizing the aqueous solution of hydrofluoric acid and spraying same upon the silica.

In both of the aforesaid embodiments the amount of hydrofluoric acid introduced into the silica will be approximately equal to the total pore volume of the silica treated.

It has also been determined that, consistent herewith, it is preferable to impregnate a silica having a specific surface ranging from about 200 to about 300 m³/g, a pore volume ranging from about 1 to about 1.5 cm³/g, an average pore diameter ranging from about 100 to 200 Å, an exchange pH less than about 3 and a sodium content, expressed in $Na_2O$, of less than about 1% by weight relative to the silica.

In another preferred embodiment of the invention, the impregnation is effected by means of an aqueous solution of hydrofluoric acid having a concentration ranging from about 0.04% to about 4% by weight.

The impregnation is preferably carried out at ambient temperature, under atmospheric pressure.

The ultimate drying is preferably carried out at a temperature ranging from about 150° to about 600° C. for about 1 to 24 hours.

Advantageously, the silica, after drying, contains a total amount of about 0.3% to about 3% by weight of fluorine.

The silica to be impregnated according hereto, containing about 0.05 to about 2% by weight of fluorine expressed as F, is conveniently obtained by the precipitation of sodium silicate by means of hydrofluoric acid.

The preparation of such silicas is described in our copending application, Ser. No. 378,192 filed concurrently herewith. The precipitation of sodium silicate with hydrofluoric acid is effected by adding an aqueous solution of hydrofluoric acid to an aqueous solution of sodium silicate, at a temperature ranging from about −50° C. to about 15° C., while maintaining a $SiO_2$ content of less than about 15% by weight of the reaction medium, until the pH of the reaction medium attains a value of about 3 to 4.5; the mixture is next allowed to gel; and the resultant hydrogel is comminuted into grains, which grains are then washed with water having a pH ranging from about 7 to about 10 and lastly dried. Approximately 1 to 1.5 mole HF is used per mole of $SiO_2$. Preferably, 40 to 50% by weight aqueous solutions of sodium silicate and hydrofluoric acid are employed. The drying is carried out for 10 to 24 hours at 150° C. to 200° C.

By "benzene radical (Ar)" as utilized herein, there is intended a phenyl radical or a phenyl radical containing one or more substituents. Exemplary of such substituents are alkyl and alkoxy radicals having from 1 to 6 carbon atoms, phenyl and phenoxy radicals, and the radicals F, $CF_3$, $OCF_3$, $SCF_3$, OH, Cl, Br or CN.

The process according to the invention is more particularly adapted to the use of compounds having Formula II or III, the phenyl radical of which bears one or more of the fluorine substituents F, $CF_3$, $OCF_3$ or $SCF_3$. In this case, a minor amount of reaction products resulting from defluorination is obtained.

The process is even more suited to the use of compounds having the Formula II and bearing a fluorine substituent. Among the latter, meta-trifluoromethylformanilide;

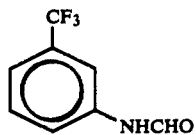

and meta-trifluoromethylbenzylformamide:

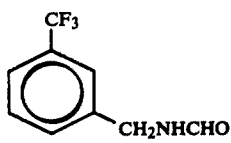

are representative; such compounds give rise to the respective preparation of meta-trifluoromethylbenzonitrile and meta-trifluoromethylphenylacetonitrile which are very important intermediates for the synthesis of a variety of compounds having phytosanitary or pharmaceutical activity. The following compounds are representative of those of Formula II suitable as starting materials in the process of the invention; formanilide, 3-trifluoromethylformanilide, 4-trifluoromethylformanilide, 4-methoxyformanilide, 4-hydroxyformanilide, 2-fluoroformanilide, 3-fluoroformanilide, 4-fluoroformanilide, 2-chloroformanilide, 3-chloroformanilide, 4-chloroformanilide, 2-chloro-5-trifluoromethylformanilide, 3-trifluoromethyl-4-chloroformanilide, 3-phenoxyformanilide, 3,5-bistrifluoromethylformanilide, 2,6-dichloroformanilide, 2,6-difluoroformanilide, 2,4-difluoroformanilide, 3-trifluoromethylthioformanilide, benzylformamide, 3-trifluoromethylbenzylformamide, 4-trifluoromethylbenzylformamide, 4-fluorobenzylformamide, 4-chlorobenzylformamide, 2-fluorobenzylformamide, 2-chlorobenzylformamide, 2-trifluoromethoxybenzylformamide, 4-trifluoromethoxybenzylformamide, 2-trifluoromethylthiobenzylformamide, 4-trifluoromethylthiobenzylformamide, 2-fluoro-5-methylbenzylformamide, 3-fluoro-6-methylbenzylformamide, 2-chloro-5-trifluoromethoxybenzylformamide, 2-trifluoromethoxy-5-chlorobenzylformamide, 2,5-difluorobenzylformamide, 2,4-difluorobenzylformamide.

An exemplary of the compounds of the Formula III are: 3-trifluoromethylbenzamide, 4-trifluoromethylbenzamide, 2-fluorobenzamide, 3-fluorobenzamide, 4-fluorobenzamide, 3-trifluoromethylphenylacetamide, 4-fluorophenylacetamide, 4-trifluoromethoxyphenylacetamide.

Thus, according to the process of this invention, the following compounds having the Formula I are conveniently prepared: benzonitrile, 3-trifluoromethylbenzonitrile, 4-trifluoromethylbenzonitrile, 4-methoxybenzonitrile, 4-hydroxybenzonitrile, 2-fluorobenzonitrile, 3-fluorobenzonitrile, 4-fluorobenzonitrile, 2-chlorobenzonitrile, 3-chlorobenzonitrile, 4-chlorobenzonitrile, 2-chloro-5-trifluoromethylbenzonitrile, 3-trifluoromethyl-4-chlorobenzonitrile, 3-phenoxybenzonitrile, 3,5-bis-trifluoromethylbenzonitrile, 2,6-dichlorobenzonitrile, 2,6-difluorobenzonitrile, 2,4-difluorobenzonitrile, 3-trifluoromethylthiobenzonitrile, 4-trifluoromethoxybenzonitrile, phenylacetonitrile, 3-trifluoromethylphenylacetonitrile, 4-trifluoromethylphenylacetonitrile, 4-fluorophenylacetonitrile, 4-chlorophenylacetonitrile, 2-fluorophenylacetonitrile, 2-chlorophenylacetonitrile, 2-trifluoromethoxyphenylacetonitrile, 4-trifluoromethoxyphenylacetonitrile, 2-trifluoromethylthiophenylacetonitrile, 4-trifluoromethylthiophenylacetonitrile, 2-fluoro-5-methylphenylacetonitrile, 3-fluoro-6-methylphenylacetonitrile, 2-chloro-5-trifluoromethoxyphenylacetonitrile, 2-trifluoromethoxy-5-chlorophenylacetonitrile, 2,5-difluorophenylacetonitrile, 2,4-difluorophenylacetonitrile.

In another, but non-critical embodiment of the invention, the reaction is carried out in the presence of a gaseous inert diluent, consisting preferably of nitrogen and/or $CO_2$ and/or acetonitrile.

It is preferred to use acetonitrile in an amount such that the molar percentage of the compound having the Formula II or III in the acetonitrile ranges from about 2 to about 20, and preferably from about 5 to about 10.

The reaction temperature preferably ranges from about 510° to 530° C. when a compound of the Formula II is employed, and from 450° to 480° C. when a compound of the Formula III is employed.

The reaction is typically conducted at atmospheric pressure, albeit pressures greater or less than atmospheric too are within the ambit of the invention.

The process according to the invention is advantageously carried out at a space velocity of from about 0.2 to about 4 moles of the compound II or III per hour and per liter of the catalyst.

The compounds III are per se known to the art and may be prepared by any known method.

Likewise, the preparation of the compounds II, when A is a direct chemical bond, is carried out in a manner well known to this prior art, by the reaction of the corresponding aniline with formic acid.

In the event that A is a hydrocarbon radical such as —$CH_2$—, the compounds II may conveniently be prepared by the reaction, at 0° to 100° C. and in the presence of hydrofluoric acid, of the corresponding benzene derivative ArH with hydroxymethylformamide, HO—$CH_2$—NHCHO. The ratio of ArH to HO—$CH_2$—NHCHO ranges from about 0.5 to about 2. Such a preparation is featured in Desbois et al copending application, Ser. No. 378,225 filed concurrently herewith and assigned to the assignee hereof.

In order to further illustrate the present invention and the advantages thereof, the following specific examples are given, it being understood that same are intended only as illustrative and in nowise limitative.

EXAMPLE I (a) Preparation of silica containing fluorine values:

A 40% solution containing 500 g HF and 2470 g water and then a second solution of sodium silicate having a density of 1.185 ($SiO_2/Na_2O = 3.3$) were prepared.

Same were both then cooled to 0° C.

The silicate solution was thereafter poured into the hydrofluoric acid solution which was being vigorously agitated, while the temperature was maintained from −2° C. to 2° C., until a pH of 4 was attained (the concentration of the silica in the resultant sol was 10.67%).

Subsequently, 2097 g of the sodium silicate solution were poured therein. The sol obtained gelled in 20 min. The hydrogel was comminuted such as to provide grains having an average diameter of 2 to 6 mm. These grains were dropped into five (5) times their volume of water over the course of one hour, the pH of the water having been adjusted to 8 by the introduction of ammonia thereto.

The solids obtained were then dried at 200° C. for 24 hours. The silica was washed with demineralized water, then dried.

The characteristics of the resultant silica were as follows:

| (i) | Specific surface | 233 | $m^2/g$ |
|---|---|---|---|
| (ii) | Total pore volume | 115 | $cm^3/100$ g |
| (iii) | Pore diameter | 115 | Å |
| (iv) | $Na_2O$ content | 1200 | ppm |
| (v) | Fluorine content | 0.16 | % |
| (vi) | Exchange pH | 3 | |

(b) Impregnation of the product silica

The silica grains prepared according to (a) were maintained for one hour in a 1% by weight hydrofluoric acid solution, and then dried for 24 hours at 200° C.

The characteristics of this particular silica were as follows:

| (i) | Specific surface, $m^2/g$ | 220 |
|---|---|---|
| (ii) | Total pore volume, $cm^3/100$ g | 15 |
| (iii) | $Na_2O$, ppm | 600 |
| (iv) | Exchange pH | 1.8 |
| (v) | Pore diameter, Å | 120 |
| (vi) | F content, % | 1.3 |

(c) Preparation of meta-trifluoromethylbenzonitrile from meta-trifluoromethylformanilide Into a stainless steel tubular reactor having a capacity of 1 liter, filled with the catalyst prepared according to the aforesaid steps (a) and (b), a mixture of 56.7 kg meta-trifluoromethylformanilide and 226.8 kg acetonitrile was continuously introduced over a period of about 450 hours. The rate of feed were adjusted over time to maintain a conversion rate of about 95%.

The reaction temperature was maintained at 520° C. throughout the catalytic bed.

After the distillation of the solvent and the water formed, the following were recovered:

(1) 37.5 kg Meta-trifluoromethylbenzonitrile;
(2) 8.9 kg Meta-trifluoromethylaniline;
(3) 3.3 kg Formanilide, unconverted; and
(4) 1.17 kg Heavy products.

Selectivity as regards the nitrile was 97.2%.

In this and the following examples, selectivity is defined as the ratio of product nitrile to the formanilide reacted, excluding the formanilide transformed into the corresponding aniline, as the latter, in an industrial process, may be quantitatively converted by means of formic acid into the beginning formanilide and recycled.

The fluoride content of the crude mixture exiting the reactor was 210 ppm.

EXAMPLE 2

(a) Impregnation of the silica prepared according to Example 1(a)

500 g of the silica prepared according to Example 1 were introduced into a rotating bowl mixer. 550 g of an aqueous solution containing 10 g HF were sprayed onto the rotating grains. The grains were then dried at 200° C. for 24 hours.

The characteristics of the product silica were as follows:

| (i) | Specific surface, $m^2/g$ | 210 |
|---|---|---|
| (ii) | Total pore volume, $cm^3/100$ g | 110 |
| (iii) | $Na_2O$, ppm | 1000 |
| (iv) | Pore diameter, Å | 120 |
| (v) | Exchange pH | 2.4 |
| (vi) | F content, % | 1.7 |

(b) Preparation of meta-trifluoromethylphenylacetonitrile from meta-trifluoromethylbenzylformamide Following the procedure of Example 1(c), a mixture of 73.8 kg meta-trifluoromethylbenzylformamide and 295 kg acetonitrile was charged over the silica obtained in Example 2(a), over the course of 500 hours and at a temperature of 520° C.

The following products were obtained after elimination of the water and the reaction solvent:

(1) 56.3 kg Meta-trifluoromethylphenylacetonitrile;
(2) 6.60 kg Meta-trifluoromethylbenzylamine;
(3) 2.43 kg Unconverted formamide; and
(4) 1.83 kg Heavy products.

Selectivity as regards the nitrile was 97.1%.

The fluorine content of the crude mixture was 210 ppm.

EXAMPLE 3

(a) Impregnation of the silica prepared according to Example 1(a)

500 g of the silica prepared according to Example 1 were introduced into a rotating bowl mixer. 550 g of an aqueous solution containing 20 g HF were sprayed onto the rotating grains. The grains were then dried at 200° C. for 24 hours.

The characteristics of the product silica were as follows:

| (i) | Specific surface, $m^2/g$ | 150 |
|---|---|---|
| (ii) | Total pore volume, $cm^3/100$ g | 115 |
| (iii) | $Na_2O$, ppm | 1200 |
| (iv) | Pore diameter, Å | 150 |
| (v) | Exchange pH | 2.8 |

| (vi) | F content, % | 1.5 |
| --- | --- | --- |

(b) Preparation of meta-trifluoromethylbenzonitrile from meta-trifluoromethylformanilide Following the procedure of Example 1(c), a mixture of 42.5 kg meta-trifluoromethylformanilide and 170.1 kg acetonitrile was charged over the silica, over the course of 450 hours. A temperature of 530° C. was maintained throughout the catalytic bed.

After distillation of the solvent and the water of reaction, the following products were recovered:
(1) 28.1 kg Meta-trifluoromethylbenzonitrile;
(2) 6.7 kg Meta-trifluoromethylaniline;
(3) 2.5 kg Unconverted formanilide; and
(4) 0.9 kg Heavy products.

The fluoride content of the crude mixture was 250 ppm.

While the invention has been described in terms of various preferred embodiments, the skilled artisan will appreciate that various modifications, substituents, omissions, and changes may be made without departing from the spirit thereof. Accordingly, it is intended that the scope of the present invention be limited solely by the scope of the following claims.

What is claimed is:

1. A process for the preparation of an aromatic or aliphatic nitrile having the formula:

Ar—A—CN    (I)

wherein Ar is a benzene radical and A is a direct chemical bond or a hydrocarbon radical having from 1 to 6 carbon atoms, comprising heating to a temperature ranging from about 450° C. to about 550° C. a formamide or formanilide having the formula:

Ar—A—NHCHO    (II)

or an amide having the formula:

Ar—A—CONH$_2$    (III)

in the presence of a fluorinated siliceous catalyst, said catalyst having been prepared by (i) impregnating a particulate silica containing from about 0.05 to about 2% by weight of fluorine, expressed as F$^-$ bonded to the silica, with a dilute aqueous solution of hydrofluoric acid, said hydrofluoric acid solution having a concentration in HF of less than about 5% by weight, and the ratio by weight of the hydrofluoric acid contained in said aqueous solution thereof to the silica being less than about 5%, followed by (ii) drying the catalyst thus impregnated.

2. The process as defined in claim 1, said impregnation (i) being carried out by soaking the silica particulates in said solution of hydrofluoric acid.

3. The process as defined by claim 1, said impregnation (i) being carried out by spraying an atomized spray of said solution of hydrofluoric acid upon said silica particulates.

4. The process as defined by claim 1, said silica particulates having a specific surface ranging from about 200 to about 300 m³/g, a pore volume ranging from about 1 to about 1.5 cm³/g, an average pore diameter ranging from about 100 to 200 Å, an exchange pH less than about 3 and a sodium content, expressed in Na$_2$O, of less than about 1% by weight relative to the silica.

5. The process as defined by claim 4, said hydrofluoric acid solution having a concentration in HF of from about 0.04% to about 4% by weight.

6. The process as defined by claim 4, said impregnation (i) being carried out at ambient temperature, under atmospheric pressure.

7. The process as defined by claim 4, said drying (ii) being carried out at a temperature ranging from about 150° C. to 600° C., for from about 1 to about 24 hours.

8. The process as defined by claim 4, said silica particulates, after the drying (ii) thereof, comprising from about 0.3% to about 3% by weight of bonded fluorine.

9. The process as defined by claim 1, wherein Ar is phenyl or phenyl substituted with at least one of the substituents, alkyl or alkoxy having from 1 to 6 carbon atoms, phenyl, phenoxy, F, CF$_3$, OCF$_3$, SCF$_3$, OH, Cl, Br and CN.

10. The process as defined by claim 9, wherein Ar is phenyl substituted with at least one of the substituents, F, CF$_3$, OCF$_3$ and SCF$_3$.

11. The process as defined by claim 1, the product nitrile having been prepared from a reactant having the formula (II).

12. The process as defined by claim 1, the product nitrile having been prepared from a reactant having the formula (III).

13. The process as defined by claim 1, with meta-trifluoromethylbenzonitrile being prepared from meta-trifluoromethylformanilide.

14. The process as defined by claim 1, with meta-trifluoromethylphenylacetonitrile being prepared from meta-trifluoromethylbenzylformamide.

15. The process as defined by claim 1, the reaction being carried out in an inert gaseous diluent.

16. The process as defined by claim 15, said inert gaseous diluent comprising nitrogen, carbon dioxide, acetonitrile, or admixture thereof.

17. The process as defined by claim 15, said inert gaseous diluent being acetonitrile, employed in an amount such that the molar percentage of the reactant (II) or (III) in the acetonitrile ranges from about 2 to about 20.

18. The process as defined by claim 4, for the preparation of one of the nitriles: benzonitrile, 3-trifluoromethylbenzonitrile, 4-trifluoromethylbenzonitrile, 4-methoxybenzonitrile, 4-hydroxybenzonitrile, 2-fluorobenzonitrile, 3-fluorobenzonitrile, 4-fluorobenzonitrile, 2-chlorobenzonitrile, 3-chlorobenzonitrile, 4-chlorobenzonitrile, 2-chloro-5-trifluoromethylbenzonitrile, 3-trifluoromethyl-4-chlorobenzonitrile, 3-phenoxybenzonitrile, 3,5-bistrifluoromethylbenzonitrile, 2,6-dichlorobenzonitrile, 2,6-difluorobenzonitrile, 2,4-difluorobenzonitrile, 3-trifluoromethylthiobenzonitrile, 4-trifluoromethoxybenzonitrile, phenylacetonitrile, 3-trifluoromethylphenylacetonitrile, 4-trifluoromethylphenylacetonitrile, 4-fluorophenylacetonitrile, 4-chlorophenylacetonitrile, 2-fluorophenylacetonitrile, 2-chlorophenylacetonitrile, 2-trifluoromethoxyphenylacetonitrile, 4-trifluoromethoxyphenylacetonitrile, 2-trifluoromethylthiophenylacetonitrile, 4-trifluoromethylthiophenylacetonitrile, 2-fluoro-5-methylphenylacetonitrile, 3-fluoro-6-methylphenylacetonitrile, 2-chloro-5-trifluoromethoxyphenylacetonitrile, 2-trifluoromethoxy-5-chlorophenylacetonitrile, 2,5-difluorophenylacetonitrile, 2,4-difluorophenylacetonitrile.

* * * * *